US011477953B2

(12) United States Patent
Whitton

(10) Patent No.: US 11,477,953 B2
(45) Date of Patent: Oct. 25, 2022

(54) METHOD OF PRODUCTION OF PHYTOCANNABINOIDS FOR USE IN MEDICAL TREATMENTS

(71) Applicant: CELL SCIENCE HOLDING LTD, Limassol (CY)

(72) Inventor: Peter Andrew Whitton, Syston (GB)

(73) Assignee: Cell Science Holding Ltd., Limassol (CY)

( * ) Notice: Subject to any disclaimer, the term of this patent is extended or adjusted under 35 U.S.C. 154(b) by 410 days.

(21) Appl. No.: 16/806,994

(22) Filed: Mar. 2, 2020

(65) Prior Publication Data

US 2020/0196548 A1 Jun. 25, 2020

Related U.S. Application Data

(63) Continuation of application No. PCT/EP2018/077149, filed on Oct. 5, 2018.

(30) Foreign Application Priority Data

Oct. 25, 2017 (GB) .................................... 1717554

(51) Int. Cl.
*A61K 36/00* (2006.01)
*A01H 4/00* (2006.01)
*C12N 5/04* (2006.01)
*A01H 3/02* (2006.01)
*A01H 6/28* (2018.01)
*A61K 31/352* (2006.01)
*A61K 36/185* (2006.01)

(52) U.S. Cl.
CPC .............. *A01H 4/005* (2013.01); *A01H 3/02* (2013.01); *A01H 6/28* (2018.05); *A61K 31/352* (2013.01); *A61K 36/185* (2013.01); *C12N 5/04* (2013.01)

(58) Field of Classification Search
None
See application file for complete search history.

(56) References Cited

U.S. PATENT DOCUMENTS

| 9,642,317 | B2 | 5/2017 | Lewis et al. |
| 2007/0151149 | A1 | 7/2007 | Karpinski |
| 2011/0209404 | A1 | 9/2011 | Scott |
| 2012/0311744 | A1 | 12/2012 | Sirkowski |
| 2017/0094920 | A1 | 4/2017 | Ellins et al. |
| 2017/0339907 | A1 | 11/2017 | Fletcher et al. |
| 2018/0070537 | A1 | 3/2018 | Vasilenko |
| 2018/0133138 | A1 | 5/2018 | Exposito Tarres et al. |
| 2018/0199531 | A1 | 7/2018 | Dawson, II |
| 2018/0258439 | A1 | 9/2018 | Boudko et al. |

FOREIGN PATENT DOCUMENTS

| CN | 1887043 | A | 1/2007 |
| CN | 106605595 | A | 5/2017 |
| CN | 106900505 | A | 6/2017 |
| CN | 107410033 | A | 12/2017 |
| CN | 107912301 | A | 4/2018 |
| CN | 108401902 | A | 8/2018 |
| WO | 2018176055 | A2 | 9/2018 |

OTHER PUBLICATIONS

Hemphill et al., The Journal of Natural Products, vol. 41, 1978, No. 5, pp. 453-461.*
International Search Report and Written Opinion; PCT Application No. PCT/EP2018/077149; dated Jan. 4, 2019.
Sayed Hussein Farag Hussein: "Cannabinoids production in *Cannabis sativa* L.: An in vitro approach Zur Erlangung des akademischen Grades eines", Jan. 1, 2014; XP055487626; Retrieved from the Internet: URL https://eldorado.tu-dortmund.de/bitstream/2003/34350/1/Dissertation.pdf.
Javier Lidoy Logrono: "In Vitro Cell Culture of Cannabis Sativa for the Production of Cannabinoids", UAB; 2014; XP002786648; Retrieved from the Internet: URL:https://ddd.uab.cat/pub/tfg/2014/119249/TFG_javierlidoylogrono.pdf.
English abstract of CN 108401902; Retreived for www.espacenet.com on Jun. 5, 2019.
English abstract of CN 107410033; Retreived for www.espacenet.com on Jun. 5, 2019.
English abstract of CN 106605595; Retreived for www.espacenet.com on Jun. 5, 2019.
English abstract of CN107912301; Retreived for www.espacenet.com on Jun. 5, 2019.
English abstract of CN 106900505; Retreived for www.espacenet.com on Jun. 5, 2019.
English abstract of CN1887043; Retreived for www.espacenet.com on Jun. 5, 2019.
Schachtsiek, J. et al., "Current perspectives on biotechnological cannabinoid production in plants",Planta Medica. 2018 v84(04), 214-220.

(Continued)

*Primary Examiner* — Michael V Meller
(74) *Attorney, Agent, or Firm* — Polsinelli PC

(57) ABSTRACT

A method of producing cannabinoids for use in medical treatments by growing cultured *Cannabis sativa* plant cells through tissue culture, the method comprising the steps of: selecting *Cannabis sativa* leaf tissue for culture; and growing a tissue culture from the selected leaf tissue in a liquid based medium whilst controlling the light exposure of the tissue culture to control the cannabinoid content of the tissue culture. Control of the light exposure can enable the phytocannabinoid content of the grown tissue culture to be tailored to the use intended for the tissue culture. For example, the THC content of the tissue culture can be controlled to be maximised or minimised depending on the intended use. Use of tissue culture is beneficial as compared to prior art methods as it allows for genetic consistency and reduces the resources necessary to produce plant cells containing phytocannabinoids.

1 Claim, No Drawings

(56) References Cited

OTHER PUBLICATIONS

Wröbel, T. et al., "The application of plant in vitro cultures in cannabinoid production", Biotechnology Letters. 2018. v40 (3), 445-454.

Lata, H. et al.; Micropropagation of *Cannabis satvia* L.—An Update in *Cannabis Satvia* L.—Botany and Biotechnology. 2017 (pp. 285-297).

Chaohua, C., "A rapid shoot regeneration protocol from the cotyledons of hemp (*Cannabis satvia* L ). Industrial Crops and Products." 2016. v83, 61-65.

Movahedi, M. et al., "Effect of explants type and plant growth regulators on in vitro callus induction and shoot regeneration of *Cannabis satvia* L.", Iranian Journal of Medicinal and Aromatic Plants 2016 v32(1), Pe83-Pe96.

Movahedi, M. et al., "In vitro callus induction and regeneration of medicinal plant *Cannabis satvia* L.", Iranian Journal of Medicinal and Aromatic Plants. 2016. v32(5), Pe758-Pe768.

Farag, S. et al., "Cannabinoids Production by Hairy Root Cultures of *Cannabis satvia* L.", American Journal of Plant Sciences. 2015. v6(11), 1874.

Feeney, Mistianne et al., "Hemp (*Cannabis satvia* L.)", In Wang, K (Ed ), Agrobacterium Protocols, vol. 2, 3rd Ed., 2015. vol. 1224, pp. 319-329).

Jiang, Y. et al., "Preliminary Studies on the Tissue culture of *Cannabis satvia* L. (Industrial hemp)", Agricultural Science & Technology. 2015. v16(5).

Raharjo, T. et al., "Callus induction and phytochemical characterization of *Cannabis satvia* cell suspension cultures", Indonesian Journal of Chemistry. 2006. v6(1), 70-74.

Lata, H. et al., "High Frequency Plant Regeneration from Leaf Derived Callus of High Δ 9-Tetrahydrocannabinol Yielding *Cannabis satvia* L.", Planta Medica 2010 v76(14), 1629-1633.

Lata, H. et al., "Propagation of elite *Cannabis satvia* for the production of D9-Tetrahydrocannabinol (THC) using biotechnological tools", Medicinal Plant Biotechnology. 2010. 98-114.

Luwanska, A. et al., "Anther culture and callus induction in *Cannabis satvia*", New Biotechnology. 2009. v25(1), 5302.

Wielgus, K. et al., "Estimation of *Cannabis satvia* L. tissue culture conditions essential for callus induction and plant regeneration", Journal of Natural Fibers. 2008. v5(3), 199-207.

Pacifico, D. et al., "Time course of cannabinoid accumulation and chemotype development during the growth of *Cannabis satvia* L", Euphytica. 2008. v160(2), 231-240.

Slusarkiewicz-Jarzina, A. et al., "Influence of cultivar, explant source and plant growth regulator on callus induction and plant regeneration of *Cannabis satvia* L", Acta Biologica Cracoviensia Series Botanica 2005 v47(2), 145-151.

Feeney, M. et al., "Tissue culture and Agrobacterium-mediated transformation of hemp (*Cannabis satvia* L.)", In vitro Cellular & Developmental Biology-Plant. 2003. v39(6), 578-585.

Mandolino, G. et al., "Hemp breeding: biotechnological aspects. II miglioramento genetico della canapa: aspetti biotecnologici", Sementi Elette. 1996. v42(2), 57-60.

Braemer, R. et al., "Biotransformation of cannabinoids by a cell suspension culture of *Cannabis satvia* L", Plant Cell Reports. 1987. v6(2), 150-152.

In vitro propagation of *Cannabis satvia*. Application to the preservation of selected clones. Multiplication vegetative in vitro du chanvre (*Cannabis satvia*L..). Application a la consevation des clones selectionnes. Agronomie. 1986. v6(5), 487-495.

Loh, W. et al., Tissue culture of *Cannabis satvia* L. and in vitro biotransformation of phenolics, Zeitschrift Fuer Pflanzenphysiologie. 1983. v111(5), 395-400.

Verzar-Petri, G. et al., "Differentiation and production of cannabinoids in tissue cultures of *Cannabis satvia*", Acta Botanica Academiae Scientiarum Hungaricae. 1982 v28(1/2), 279-290.

Braut-Boucher, F. et al., "Tissue culture of different chemical types of *Cannabis satvia* L. Sur la mise en culture in vitro de tissus de differents types chimiques du *Cannabis satvia* L", Comptes Rendus Hebdomadaires des Seances de l'Academie des Sciences, III. 1981. v292(13), 833-838.

Hemphill, J. et al., "Studies on growth and cannabinoid composition of callus derived from different strains of *Cannabis satvia*", Lloydia. 1978. v41(5), 453-462.

Itokawa, H. et al., "Biotransformation of Cannabinoid Precursors and Related Alcohols by Suspension Cultures of Callus Induced From *Cannabis satvia* L", Chemical & Pharmaceutical Bulletin. 1977. v25(8), 1941-1946.

Culberson, E., "A Primer On Tissue culture", Apr. 4, 2018, Cannabis Business Times. 2018; URL: http://www.cannabisbusinesstimescom/article/a-primer-on-tissue-culture/.

Alamgir, A. et al., "Cultivation of Herbal Drugs, Biotechnology, and In vitro Production of Secondary Metabolites, High-Value Medicinal", Plants, Herbal Wealth, and Herbal Trade in Therapeutic Use Of Medicinal Plants And Their Extracts: vol. 1: Pharmacognosy. 2017, (vol. 73, pp. 379-452).

Grulichova, M. et al., "Effect of Different Phytohormones on Growth and Development of Micropropagated *Cannabis satvia* L. Conference Paper in Cerkal, R and Belcredi, NB and Prokesova, L and Vacek, P (Ed.)", Proceedings of 24th International PHd Students Conference (MendeInet2017). 2017. (pp. 618-623).

Lata, H. et al., "In vitro mass propagation of *Cannabis satvia* L.: A protocol refinement using novel aromatic cytokinin meta-topolin and the assessment of eco-physiological, biochemical and genetic fidelity of micropropagated plants (a)", Journal of Applied Research on Medicinal and Aromatic Plants. 2016. v3(1), 18-26.

Lata, Chandra H. et al., "In vitro germplasm conservation of high Delta(9)-tetrahydrocannabinol yielding elite clones of *Cannbis satvia* L. under slow growth conditions", Acta Physiologiae Plantarum. 2012. v34(2), 743-750.

Lata, H. et al., "Assessment of Cannabinoids Content in Micropropagated Plants of *Cannabis satvia* and Their Comparison with Conventionally Propagated Plants and Mother Plant during Developmental Stages of Growth", Planta Medica. 2010. v76(7), 743-750.

Lata, H. et al., "Propagation of Elite *Cannabis satvia* L. for the Production of Delta(9)-Tetrahydrocannabinol (THC) using Biotechnological Tools", In Arora, R (Ed ), Medicinal Plant Biotechnology. 2010. (pp. 98-114).

Flores-Sanchez, I. et al., "Elicitation studies in cell suspension cultures of *Cannabis satvia* L", Journal of Biotechnology. 2009. v143(2), 157-168.

Bing, X. et al., "Rapid tissue culture method of *Cannabis satvia* for industrial uses", CN. 2007. v1887043: 9.

Feeney, M., "Tissue culture of American Ginseng, *Panax quinquefolius* L., and Hemp, *Cannabis satvia* L., and Agrobacterium-mediated Transformation of Hemp (MSc)", MSc Thesis Simon Fraser University 2002.

Veliky, I. et al., "Growth and Metabolites Of *Cannabis satvia* Cell suspension cultures", Lloydia—The Journal of Natural Products. 1972. v35(4), 450-456.

Stevens, M., An Exclusive Look at Cannabis Tissue culture, a Transformative Technology—Part 1. (n.d.).

\* cited by examiner

METHOD OF PRODUCTION OF PHYTOCANNABINOIDS FOR USE IN MEDICAL TREATMENTS

CROSS-REFERENCE TO RELATED APPLICATIONS

This application is a continuation of prior PCT application No. PCT/EP2018/077149 filed Oct. 5, 2018, which claims the benefit of UK application number GB1717554.8 filed Oct. 25, 2017, each of the aforementioned applications is expressly incorporated herein by reference in their entirety.

BACKGROUND TO THE INVENTION

Phytocannabinoids are a set of compounds present in cannabis plants that, when ingested, interact with the human body to produce a physical or psychological effect. The best known phytocannabinoid is tetrahydrocannabinol (THC). Phytocannabinoids are becoming increasingly commonly used in medical treatments under the umbrella term of medical marijuana. This term covers the use of any phytocannabinoid in order to treat a physical or mental condition. Medical marijuana is an active and growing sector and as such there is need for a reliable and consistent source of phytocannabinoids.

Currently phytocannabinoids for use as medical marijuana are generally obtained from *Cannabis Sativa* plants that are grown in a conventional agricultural manner. However, the growth of *Cannabis Sativa* plants in this manner is less than ideal. The plants will always have variations in phytocannabinoid content, even if cultivated in identical conditions, due to natural genetic variations between plants. Further, variations between weather and/or soil conditions during agricultural growth of plants can lead to variation in phytocannabinoid contents of the plants.

Land use is as a problem as it takes land out of use for alternative uses, such as conventional agriculture. Land security can also be a problem as cannabis plants are valuable to third parties for legal and non-legal uses. Agricultural cannabis cultivation also requires large quantities of water and is a relatively inefficient process.

As an alternative to conventional agricultural growth, cannabis plants are often grown hydroponically indoors. However, such growth is extremely energy intensive and requires large quantities of water. As the plants require artificial lighting in indoor situations it is also necessary for the ventilation and temperature control to be provided to remove excess heat produced by the lighting. Further, the issue of genetic variation remains present in hydroponically grown plants.

In light of the above there is a need for a new method of producing phytocannabinoids that is secure, reduces the resource requirements, and can provide consistent amounts of phytocannabinoids.

SUMMARY OF THE INVENTION

The present invention provides a method of producing phytocannabinoids for use in medical treatments by growing cultured *Cannabis sativa* plant cells through tissue culture, the method comprising the steps of:
  selecting *Cannabis sativa* leaf tissue for culture; and
  growing a tissue culture from the selected leaf tissue in a liquid based medium whilst controlling the light exposure of the tissue culture to control the cannabinoid content of the tissue culture.

The method of the present invention is advantageous as it allows production of a medium of consistent and controllable phytocannabinoids content. In particular, tissue culture allows production of tissue without genetic variation and control of light exposure allows control of phytocannabinoid production within the tissue. The leaf tissue that is cultured can be selected to provide the correct phytocannabinoid composition. For example, a leaf tissue that provides maximised or minimised levels of THC and/or cannabis oil may be selected.

After growth of the tissue culture the resulting cells can either be used directly as a medicament or the phytocannabinoids can be extracted from the cells for further processing. In contrast to previous methods, the tissue culture produced by the method of the present invention has consistent phytocannabinoid content that can be controlled and, as such, it is possible to use the plant cells of the tissue culture as a medicament without further significant processing. For example, the plant cells of the tissue culture may be freeze-dried and used as a medicament without any further processing or by subsequently dissolving the freeze-dried cells in water.

Phytocannabinoids produced by the method of the present invention may be used in many dosage forms including but not limited to tablets, capsules, lozenges, vapour inhalation products or other orally taken dosage forms.

In order for the tissue culture of the present to grow it is necessary that the tissue culture is exposed to photosynthetically active radiation (PAR). As will be readily understood PAR is light that allows the tissue to photosynthesise. Generally, photoreceptors for photosynthesis are most efficient in the blue (400-500 nm) and red (600-700 nm) area of the light spectrum. Far-red, (700-800 nm) is critical for flowering of many plants.

The (500-600 nm) green area is less understood and even though much of this range is reflected, it is considered beneficial for carotenoids and lycopene (for colour and photo-protection). On that basis, most PAR will comprise blue and red light and may also comprise far-red and/or green light. There are many commercially available lighting systems that are designed and intended for producing PAR for plant growth and that would be suitable for use in the method of the present invention.

In embodiments of the invention the light exposure may be controlled such that tissue culture is constantly exposed to PAR during growth of the tissue culture. This can be beneficial as it can maximise the growth of the tissue culture. In particular, as the method of the present invention involves the growth of tissue culture, rather than whole plants, there is no requirement for the PAR to be cycled to replicate natural daylight cycles.

In order to grow the tissue culture sufficiently it is generally preferred that the PAR is controlled to provide at least 0.2 moles of photons per day, and preferably 0.5 moles of photons per day. The precise amount of PAR provided in any embodiment of the method of the present invention will be dependent on the amount of tissue culture that is exposed to the PAR. A larger amount of tissue culture will generally require a larger amount of PAR in order to grow sufficiently.

Whilst PAR is required to grow the tissue culture, the control of phytocannabinoids in the tissue culture can be controlled by controlling the exposure of the tissue culture to UV light. In particular, it is believed that phytocannabinoids, including THC, are formed in cannabis to protect the plant from UV light as each THC molecule has several ring structures that act to protect the plant from UV light. Therefore, exposure to UV light is believed to increase the production of THC in cannabis plants and the same mechanism would occur in cannabis tissue culture.

In order to increase the production of THC and other phytocannabinoids in the tissue culture, in embodiments of the present invention the light exposure is controlled such that the tissue culture is exposed to UV light during growth of the tissue culture. In alternative embodiments in order to minimise the production of THC and other phytocannabinoids in the tissue culture the light exposure may be controlled such that exposure of the tissue culture to UV light is minimised. However, UV radiation is important in inducing production of phenolics, anthocyanins (colouration), antioxidants and vitamins that inhibit mold growth in the tissue culture. Therefore, it may be necessary that the tissue culture is exposed to a relatively small amount of UV radiation in order to allow the tissue to generate such chemicals. For example, if UV radiation is minimised it may be controlled such that the tissue culture is exposed to less than 0.05 moles of photons per day.

Maximised THC content may be preferred if the tissue culture is being grown in order to produce THC for use in the treatment of chronic pain or other similar conditions. Minimised THC content may be preferred if the tissue culture is being grown in order to produce cannabis oils for use in the treatment of Parkinson's disease.

UVA light, consisting of light of wavelength 315-400 nm, may result in increased levels of THC, other phytocannabinoids, and other chemicals crucial to tissue growth. Therefore, it may be preferable that the light exposure is controlled such that the tissue culture is exposed to UVA light during growth of the tissue culture.

Exposire to UVB light, consisting of light of wavelength 280-315 nm results in increased production of THC, other phytocannabinoids, and other chemicals crucial to tissue growth within the cannabis plant. Therefore, it may be preferable that the light exposure is controlled such that tissue culture is exposed to UVB light during growth of the tissue culture. It is generally believed that UVB light is more effective than UVA light in increasing levels of THC within cannabis. Therefore, it may be preferable that the levels of UVB light are maximised in methods according to the present invention where high THC levels are desired and that levels of UVB light are minimised in methods according to the present invention where low THC levels are desired.

In order to maximise THC levels in the tissue culture it can be generally beneficial to maximise the intensity of UV light to which the tissue culture is exposed. However, intensities of UV light that are too high can damage the tissue culture. In particular, constant exposure of UV light at intensities of 1200 lumens and above can damage a tissue culture, whilst even periodic exposure to UV light at intensities above 2000 lumens can damage the tissue culture. Therefore, in embodiments of the present invention it may be preferable that the UV light is controlled during growth of the tissue culture such that the tissue culture is exposed to UV light of an intensity greater or equal to 1200 lumens but less than 2000 lumens and the UV light exposure is cycled through alternating periods of exposure and darkness; wherein each period of exposure is at least 30 minutes and each period of darkness is at least 30 minutes. Each period of exposure to UV light may be equal to or less than one hour and each period of darkness may be equal to or less than one hour. Advantageously, each period of exposure to UV light will be followed by a period of darkness that is equal in duration to the previous period of exposure to UV light. It may also be advantageous that each period of exposure of UV light is of equal duration.

In relation to the period exposure of the tissue culture to UV light it is to be understood that the a period of darkness is a period in which the tissue culture is exposed to substantially no UV light but it may still be exposed to normal PAR or other light. That is in this context "darkness" is to be understood to mean the substantial absence of UV light.

In alternative embodiments of the method of the present invention the UV light is controlled during growth of the tissue culture such that the tissue culture is constantly exposed to UV light of an intensity equal to or less than 1200 lumens, or equal to or less than 600 lumens.

During growth of the tissue culture it is preferable that the tissue culture is maintained at an optimum temperature to promote tissue growth. For example, the tissue culture may be maintained at a temperature between 25° C. and 30° C., for example 27° C.

In the method of the present invention the tissue culture may be grown for any suitable period of time in order to allow for the desired amount of tissue culture to be grown. For example, the tissue culture may be grown for between 10 and 28 days. In embodiments of the invention the tissue culture may be grown for 14 days.

In order to promote growth of the tissue culture it may be preferable that the tissue culture is agitated during its growth, for example by positioning the tissue culture on a shaker during the growth.

It may also be preferable that the $CO_2$ content of the environment in which the tissue culture is grown is controlled to increase tissue growth. This can be done in any manner apparent to the person skilled in the art.

The tissue culture produced by the method of the present invention may be used in any suitable way. For example, the method may further comprise the step of collecting and freeze-drying the tissue culture after growing. The freeze-dried tissue culture may then be used as a medicament or as part of a medicament. Alternatively, the desired active ingredient, for example THC or any other phytocannabinoid, may be extracted from the tissue culture after growth.

In order to provide consistency in the method of the present invention it may be advantageous that some or all of the leaf tissue culture selected for culture was previously grown according to the method of the present invention. That is, genetic consistency can be assured by continuing to use the same tissue culture for subsequent tissue culture growth after an initial run of the method of the present invention.

During growth of the tissue culture it can be preferable that air is added to the liquid based medium in order to keep the tissue cells oxygenated. For example, it may be preferable to keep the saturated oxygen level above 20%, or more preferably 25%, in the liquid based medium.

Any suitable liquid based medium may be used to grow the tissue culture. In embodiments of the invention the liquid based medium may be formed of a Murashige and Skoog solution, with potential further additions to adjust the pH level and/or with the potential addition of sucrose or an equivalent substance.

An example of an embodiment of the method of the present invention is described below. It is to be understood that this is provided as an example only and is not intended to be limiting on the scope of the application. Unless specifically indicated any specific step of the method may be used in any method of the present invention.

EXAMPLE i) Liquid Media

Starting Media
0.44% Murashige and Skoog basal powdered medium
1.0% NAA (naphthalene acetic acid) 0.004% stock solution
3.0% sucrose
Distilled water to 100%

Equipment
Glass bottle with cap
Magnetic stirrer
Sterile plastic plant culture dishes
Glass pipettes
pH meter
Autoclave
Laminar flow cabinet
Balance
Nescofilm
Phytagel
1M NaOH solution
0.1M NaOH solution The liquid media was prepared in the following manner:

a) The starting media was Murashige and Skoog (MS) media with 3% sucrose and 1% naphthalene acetic acid (from concentrated stock solution of 0.004% w/v);

b) The media was then pH adjusted to pH 5.75 and solidified with 0.2% phytagel;

c) The media was then autoclaved for 20 minutes at 121° C. and then poured into sterile plastic plant tissue culture dishes.

ii) Culture Initiation

Reagents
Liquid media (as prepared in the manner set out above)
*Cannabis sativa* leaf tissue
Equipment
Sterile glass beakers
Sterile distilled water
Sterile scalpel
Sterile tweezers
10% bleach solution
70% ethanol solution
1M NaOH solution
0.1M NaOH solution The culture was initiated in the following manner:

a) The leaf tissue of *Cannabis Sativa* was sterilised by immersion in 70% ethanol for 2 minutes, followed by immersion in 10% bleach solution for 10 minutes;

b) The leaf tissue was then washed three times with sterile (autoclaved) distilled water;

c) The sterile washed leaf tissue was aseptically cut into disc shapes in a sterile laminar flow cabinets;

d) The leaf tissue slices were placed onto the prepared plates containing callus induction media, and plates were sealed with Nescofilm®.

e) The plates were placed in the dark at 27° C. and callus formation began to appear after about 1 month.

iii) Media Preparation for Cultures

Reagents
3% sucrose
0.44% Murashige and Skoog basal powdered medium
1% naphthalene acetic acid (NAA) 0.004% stock solution
0.01% vitamin solution (0.05% pyridoalhydrochlorid, 0.1% thiamine dichloride, and
0.05%g nicotinic acid)
1M NaOH solution
0.1M NaOH solution
Distilled water to 100%
Equipment
1L glass bottle
Magnetic stirrer
20×250 m conical
20 sheets of foil approximately 20 cm×20 cm
Glass pipettes
pH meters
Autoclave
Laminar flow cabinet
Balance The media was prepared in the following manner:

a) Mix 3% sucrose, 0.44% Murashige and Skoog basal powder, 1% NAA stock, and 0.01% vitamin solution and prepare to 100% with distilled water;

b) Mix using a magnetic stirrer until all dry components dissolved, then pH adjust with 1M and 0.1 M NaOH to a pH of 5.75;

c) Take 20×250 ml conical flasks, to each add 50 ml media and seal neck of flask with foil; sterilize in autoclave at 121° C., 103 kPa for 25 minutes;

d) Immediately following sterilization place flasks in laminar flow cabinet and allow to cool to ambient temperature.

iv) Inoculation and Subculture of Established Cultures

Reagents
Friable callus
70% ethanol
Equipment
Laminar flow cabinet
Bunsen burner
Prepared media
20 sterile sheets of foil approximately 20 cm×20 cm
Several pairs of tweezers or small forceps
Wide spatulas with holes
Broad spectrum PAR lighting
UVA and UVB lighting The inoculation and subculture of established cultures was carried out in the following manner:

a) Sterilize inside of laminar flow cabinet with 70% ethanol;

b) Sterilize all tweezers and spatulas by dipping in 70% ethanol, then flaming till red hot. Allow to cool inside laminar flow cabinet;

c) Remove foil from prepared media flask;

d) Take sterilized tweezers and remove thumbnail sized pieces of friable callus from the plant tissue. Break up into finely dispersed cells and add to flask. Aim to add approximately 5 g of tissue to 50 ml media (10% w/v);

e) Flame the neck of the flask and cover with a sterile sheet of foil;

f) Place the flask on a shaker at 120 rpm, in a dark room heated to 27° C. Leave until a thick dispersed cell suspension culture can be observed, approximately 2 weeks;

g) Remove foil from prepared media flask;

h) Remove foil from flask containing dispersed cell suspension cultures (produced by inoculation at point f);

i) Take wide spatula with holes, sterilize, allow to cool, and scoop out the cells.

Add these cells to the fresh media. Aim to add approximately 5 g tissue to 50 ml of media;

j) Flame the neck of the flask and cover with a sterile sheet of foil;

k) Place the flask on a shaker at 120 rpm in, subject to one of the two lighting regimes set out below, and heated to 27° C. for 14 days; and l) After 14 days use the cell suspension culture for further subcultures or harvest cells.

Lighting Regime 1

Constant exposure to PAR at a rate of 0.5 moles of photons per day; and

Constant exposure to UVB and UVA radiation at an intensity of approximately 500 lumens.

Lighting Regime 2

Constant exposure to PAR at a rate of 0.5 moles of photons per day; and

Periodic exposure to UVB and UVA radiation at an intensity of approximately 1500 lumens, the periodic exposure consisting of alternating 1 hour periods of exposure and 1 periods in which there is no UVB and UVA exposure.

The invention claimed is:

1. A method of controlling the tetrahydrocannabinol content of a tissue culture, the method comprising the steps of:
    a) selecting *Cannabis sativa* leaf tissue for culture; and
    b) growing a tissue culture for between 10-28 days from the selected *cannabis sativa* leaf tissue in a liquid based medium comprising Murashige and Skoog basal powdered medium and a callus induction media while controlling the ultraviolet light exposure of the tissue culture to control the tetrahydrocannabinol content of the tissue culture, wherein the ultraviolet light is controlled during growth of the tissue culture such that the tissue culture is exposed to ultraviolet light of an intensity greater or equal to 1200 lumens but less than 2000 lumens and the ultraviolet light exposure is cycled through alternating periods of exposure and darkness and wherein the light exposure is controlled such that tissue culture is constantly exposed to photosynthetically active radiation to provide at least 0.5 moles of photons per day, wherein each period of exposure is at least 30 minutes and each period of darkness is at least 30 minutes, wherein the carbon dioxide content of the environment in which the tissue culture is grown is controlled to increase tissue growth, wherein the selected *cannabis sativa* leaf tissue of step a) was previously grown in a liquid based medium while controlling the light exposure of the tissue culture to control the tetrahydrocannabinol content of the tissue culture and wherein the tissue culture is exposured to ultraviolet B light, consisting of light of wavelength 280-315 nm which results in increased production of tetrahydrocannabinol and callus formation begins after about one month of culturing.

* * * * *